United States Patent [19]

Giambattista et al.

[11] Patent Number: 5,549,575

[45] Date of Patent: Aug. 27, 1996

[54] CARTRIDGE RETAINER ASSEMBLY FOR MEDICATION DELIVERY PEN

[75] Inventors: Lucio Giambattista, East Hanover; Theodore Siuta, Brant Beach, both of N.J.

[73] Assignee: Becton Dickinson and Company, Franklin Lakes, N.J.

[21] Appl. No.: 304,953

[22] Filed: Sep. 13, 1994

[51] Int. Cl.⁶ .................................................. A61M 5/00
[52] U.S. Cl. ............................ 604/232; 604/206; 604/241
[58] Field of Search ...................................... 604/232, 234, 604/206–211, 240–243, 181, 187, 199–201, 71, 72, 131–136, 139, 218, 905

[56] References Cited

U.S. PATENT DOCUMENTS

| | | | |
|---|---|---|---|
| 4,973,318 | 11/1990 | Holm et al. | 604/208 |
| 5,041,088 | 8/1991 | Ritson et al. | 604/135 |
| 5,085,641 | 2/1992 | Sarnoff et al. | 604/135 |
| 5,281,198 | 1/1994 | Haber et al. | 604/232 |
| 5,360,410 | 11/1994 | Wacks | 604/205 |

*Primary Examiner*—John D. Yasko
*Assistant Examiner*—Ronald K. Stright, Jr.
*Attorney, Agent, or Firm*—Alan W. Fiedler

[57] ABSTRACT

A cartridge retainer assembly is provided for a medication delivery pen. The cartridge retainer assembly includes a generally tubular body for receiving, supporting and accurately positioning the body and shoulder portions of a cartridge of medication. A needle mounting collar is floatably mounted to the body of the cartridge retainer assembly for receiving the neck, rubber septum and crimped metallic sleeve of the cartridge. The needle mounting collar will float into a position which compensates for eccentricities and dimensional variations of the cartridge.

9 Claims, 5 Drawing Sheets

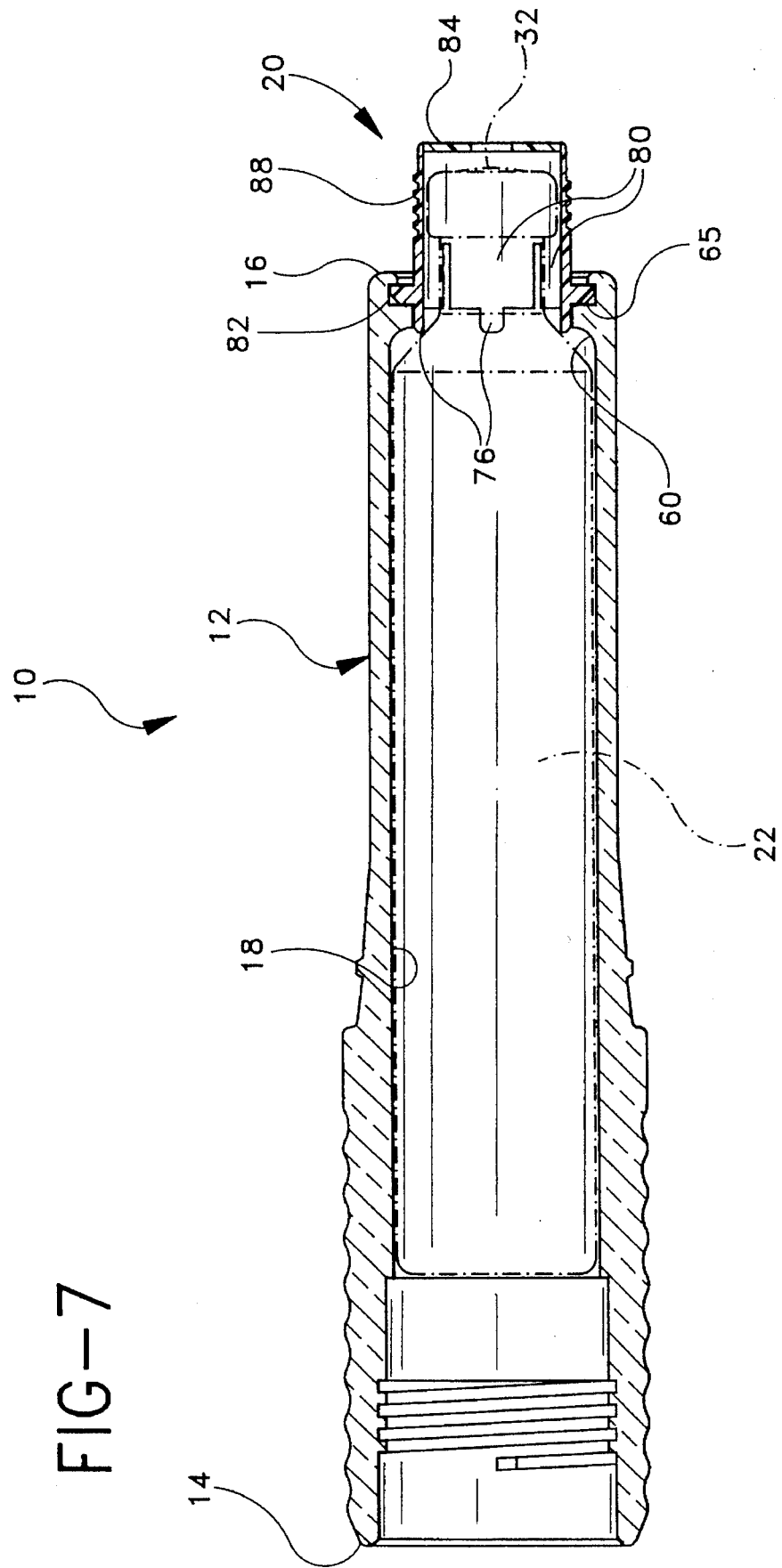

CARTRIDGE RETAINER ASSEMBLY FOR MEDICATION DELIVERY PEN

BACKGROUND OF THE INVENTION

1. Field of the Invention

The subject invention relates to the portion of a medication delivery pen that retains the cartridge of medication.

2. Description of the Prior Art

Medication delivery pens are hypodermic syringes that are used for self-injection of precisely measured doses of medication. Pens are widely used, for example, by diabetics to dispense insulin.

The typical prior art medication delivery pen includes a cartridge which contains a volume of liquid medication sufficient for several doses. The prior art cartridge includes an elongated generally tubular glass vial having an open proximal end and an opposed open distal end. The vial includes a large diameter barrel extending distally from the open proximal end to an inwardly tapering shoulder between the two ends. A short small diameter neck extends from the shoulder to the open distal end. The neck of the prior art vial has an annular rim projecting outwardly around the extreme distal end.

The prior art cartridge further includes a pierceable rubber septum which extends across the open distal end of the prior art vial, and is securely held in position by a metallic sleeve that is crimped to the annular rim on the tubular neck. The vial of the prior art cartridge is filled with liquid medication, and a rubber stopper is inserted into the open proximal end of the vial for sliding fluid-tight engagement with interior walls of the barrel.

The prior art medication delivery pen includes a unitarily molded cartridge retainer with opposed proximal and distal ends. A large diameter tubular body extends distally from the proximal end and is dimensioned for receiving the barrel of the vial. A short smaller diameter tubular neck is disposed distally of the body and is dimensioned for tightly engaging the tubular neck of the vial and the metallic sleeve crimped thereon so as to support and position the entire cartridge. Exterior regions at the extreme distal end of the tubular neck are formed with an array of threads for threadedly receiving the mounting cap of a needle assembly.

The prior art medication delivery pen further includes a dosing apparatus that is engaged with the proximal end of the cartridge retainer. The prior art dosing apparatus includes a plunger for engaging the rubber stopper of the cartridge, dose setting structure for selecting the longitudinal distance through which the plunger will move, and dispensing means for driving the plunger the selected distance. The prior art dosing apparatus may be permanently connected to prior art cartridge retainer with the cartridge therein. This type of prior art pen is used until the medication is exhausted and then the entire pen is discarded. Other prior art medication delivery pens may have the dosing apparatus removably connected to the cartridge retainer so that at least portions of the pen may be reused when the medication in the cartridge is exhausted.

Prior art needle assemblies for medication delivery pens are safely sealed in packages. A needle assembly is accessed immediately prior to an injection, and is discarded immediately after the injection. The prior art needle assembly for medication delivery pens includes an elongate needle cannula having opposed proximal and distal points and a lumen extending therethrough. A plastic cork is adhered to an intermediate position along the needle cannula and in turn is rigidly connected to an end wall of a cylindrical cap. The cylindrical wall of the cap surrounds the proximal point on the needle cannula and includes an array of internal threads for engaging the external threads on the neck of the prior art cartridge retainer.

The prior art medication delivery pen may be used by opening the sealed needle assembly and urging the cap over the neck of the vial retainer sufficiently for the proximal point of the needle cannula to pierce the rubber septum of the prior art cartridge. The cap is then rotated to threadedly engage the neck of the prior art cartridge retainer. The user will then manipulate the dosing apparatus to select an appropriate dose. A protective shield over the distal end of the needle cannula is then removed, and the distal point of the needle cannula is injected. The user then actuates the dispensing means of the prior art dosing apparatus to urge the stopper of the cartridge distally and to deliver medication through the lumen of the needle cannula. The needle is then withdrawn, and the needle assembly is separated from the cartridge retainer and safely discarded. The rubber septum of the cartridge will reseal itself, and may be pierced again for a subsequent administration of medication. This process may be carried out repeatedly until all of the medication in the cartridge has been used.

The neck at the distal end of the prior art unitarily molded cartridge retainer has been precisely formed to closely engage, support and position the entire cartridge. However, cartridges are subject to a considerable range of dimensional variations and a considerable degree of eccentricity. These dimensional variations and eccentricities may be due to the glass vial manufacturing processes or to the crimping of the metallic sleeve that holds the rubber septum in place. Dimensional variations can result in a cartridge that will not fit the cartridge retainer or that will be loosely supported and movable therein. Eccentricities can result in a vial barrel that is not properly positioned or aligned within the body of the cartridge retainer. Eccentricities also can prevent the neck of the vial from sliding into the precisely dimensioned neck of the cartridge retainer. As a result, considerable quality control efforts must be undertaken to ensure that only cartridges that are within narrowly defined dimensional tolerances are used, and high reject rates occur. To reduce rejects and ensure that a larger number of vials can be accepted, prior art pens have included vial retainers with wider bodies that are intended to accommodate a greater range of eccentricities between the neck and the body of the vial. This results in larger pens even though it would be desirable to reduce the size.

Users of medication delivery pens are urged to disinfect both the puncture site and the distal end of the pen prior to each injection of medication. The disinfectant can react with the plastic of the prior art cartridge retainer to cause crazing or cracking.

Medication delivery pens also have been found to exhibit weeping or drooling near the interface of the needle assembly and the cartridge retainer. This weeping or drooling presents inconveniences to the user and creates the potential for an accumulation of medication at an external position on the pen and near the puncture site of the patient.

It is now believed that weeping or drooling is attributable to contact between the septum and the cork of the needle assembly during the injection of medication. In particular, the movement of the plunger distally in the vial urges the liquid in a distal direction. These distally directed forces urge liquid through the lumen of the needle cannula. However, these forces also cause a stretching of the septum in a distal direction. As noted above, the neck of the prior art cartridge retainer provides the primary support for the cartridge, and hence closely engages the metal sleeve which holds the septum to the vial. The distal stretching of the septum in response to fluid pressure urges the septum into direct contact with the cork on the needle assembly of the prior art medication delivery pen. The combination of fluid pressure and contact with the cork will sufficiently change the shape of the pierced septum to permit the weeping or drooling of medication between the septum and the needle cannula.

Still another problem with prior art medication delivery pens relates to the above described disposition of threads around the distal end of the prior art cartridge retainer. In particular, the threads begin at the distal tip of the prior art cartridge retainer and extend a short distance in a proximal direction. Even minor variations in dimensional tolerances can require the user to threadedly engage the cap of the needle assembly to the threads of the cartridge retainer before the proximal tip of the needle cannula has pierced the septum. In these instances, the beveled proximal tip of the needle cannula will pierce the septum while undergoing a rotational movement. This may cause the beveled tip to rip the septum and may further contribute to the above described drooling or weeping. Sufficiently large rips may not adequately reseal and can lead to a premature degradation of the medication stored in the vial.

SUMMARY OF THE INVENTION

The subject invention is directed to a two-piece cartridge retainer assembly that is particularly suitable for medication delivery pens. The cartridge retainer assembly includes a generally tubular body for surrounding the barrel of a vial and for supportingly engaging the converging wall that defines the shoulder of the vial. The cartridge retainer assembly further includes a needle mounting collar floatingly mounted to the body for surrounding the neck of the vial. The needle mounting collar may be diametrically dimensioned to closely engage the metallic sleeve which is crimped to the vial for holding the rubber septum in place. However, such close engagement is not essential. The needle mounting collar of the cartridge retainer assembly may also define an axial length for preventing contact between the rubber septum and the cap or cork of the needle assembly. Thus, drooling or weeping in response to contact between a distended septum and the cork of the needle assembly is substantially eliminated.

Floating between the needle mounting collar and the body of the cartridge retainer assembly enables the cartridge retainer assembly to accommodate a much greater range of eccentricities. Hence, the diametrical dimensions of the body of the cartridge retainer assembly can be reduced. Additionally, the two-piece design for the cartridge retainer assembly enables dissimilar materials to be used for the body and the needle mounting collar. For example, the body may be formed from any convenient transparent plastic material that will provide the necessary structural support and that will enable observation of the stopper positioned within the vial. The needle mounting collar, on the other hand, may be formed either from a thin metal or a plastic that exhibits appropriate resistance to disinfectants that may be used before or after each injection.

The secure but floatable connection of the needle mounting collar to the body may be achieved by a plurality of axial extending slots formed either on the body or the needle mounting collar of the cartridge retainer. The slots may define resiliently deflectable fingers. Each finger may be provided with tabs disposed and dimensioned to be snap fit into corresponding grooves in the opposing member. The tabs and grooves will prevent unintended axial separation of the needle mounting collar and the body of the cartridge retainer assembly. However, the resiliently deflectable fingers will permit a certain range of radial movement to accommodate dimensional variations and eccentricities in the cartridge being retained. Preferably the external threads on the needle mounting collar of the cartridge retainer assembly are spaced proximally from the extreme distal end. This proximal position ensures that the proximal tip of the needle cannula can pierce the septum in response to axial movement of the needle assembly and without relative twisting that could cause ripping of the septum. The twisting for threaded engagement of the needle assembly and the needle mounting collar will be carried out only after the beveled tip is fully within the vial and beyond the position where rotation of the needle can urge the sharp beveled edges into ripping or tearing engagement with the rubber septum.

BRIEF DESCRIPTION OF THE DRAWINGS

FIG. 7 is a cross-sectional view taken along line 7—7 in FIG. 2.

DETAILED DESCRIPTION OF THE PREFERRED EMBODIMENT

Figure 1:
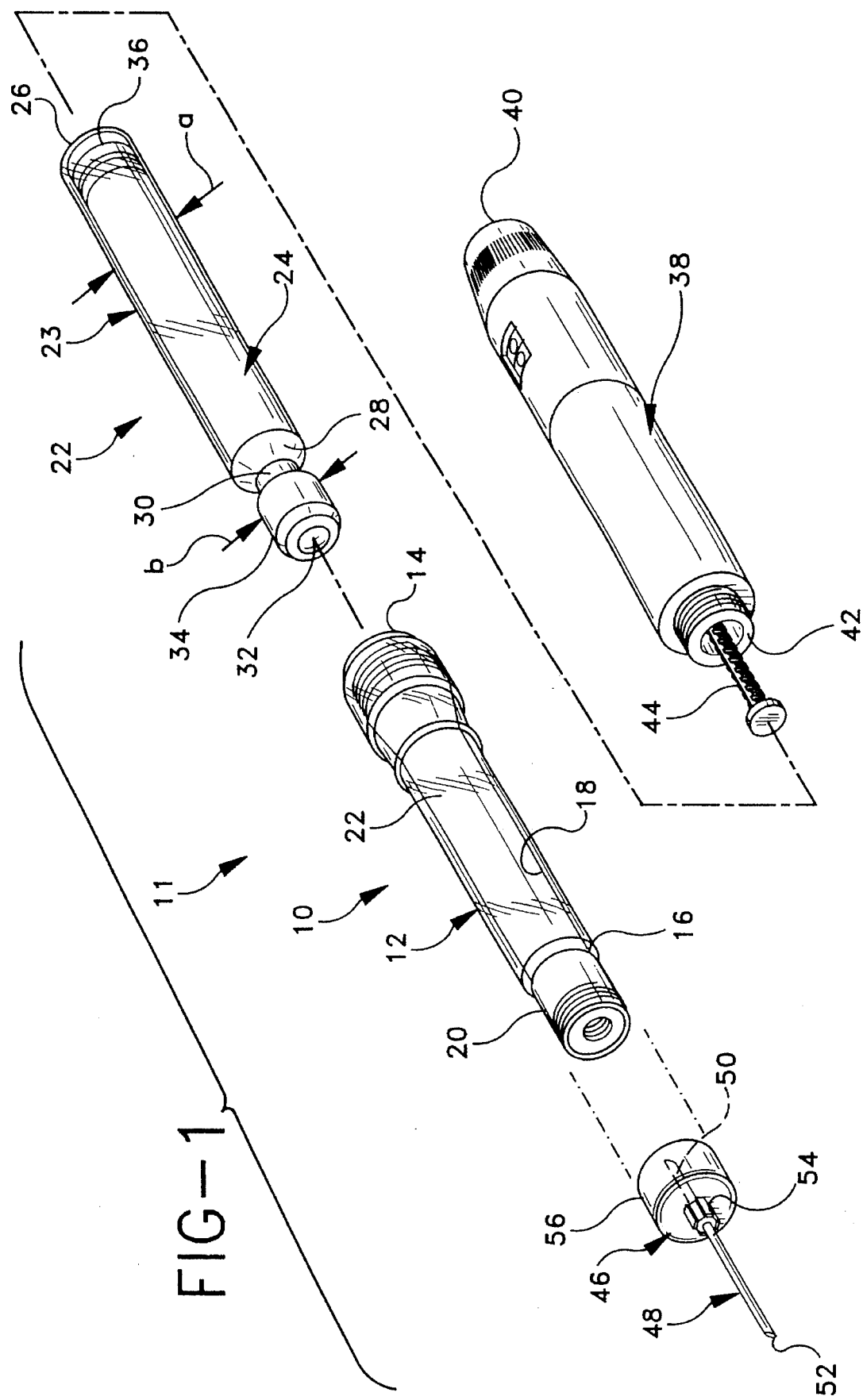
FIG. 1 is an exploded perspective view of a medication delivery pen having a cartridge retainer assembly in accordance with the subject invention.

A cartridge retainer assembly in accordance with the subject invention is identified generally by the numeral 10 in FIGS. 1–7. Cartridge retainer assembly 10 is intended to be a part of a medication delivery pen 11 and includes elongate generally tubular body 12 with opposed proximal and distal ends 14 and 16 respectively and a cartridge receiving cavity 18 extending therebetween. A generally tubular needle mounting collar 20 is floatably mounted to distal end 16 of body 12. Body 12 and collar 20 of cartridge retainer assembly 10 both are described in greater detail below.

Cartridge retainer assembly 10 is dimensioned and configured to receive a cartridge assembly 22 therein. Cartridge assembly 22 includes a vial 23 with a generally tubular barrel 24 of diameter "a" with an open proximal end 26 and a distal end defined by an inwardly converging shoulder 28. A small diameter neck 30 projects distally from shoulder 28 of barrel 24 on vial 23, and is provided with a large diameter annular bead (not shown) extending circumferentially thereabout at the extreme distal end of neck 30. A pierceable and resealable rubber septum 32 extends completely across the open distal end defined by neck 30. Rubber septum 32 is held in place by a metallic sleeve 34 which is crimped around the circumferential bead at the distal end of neck 30. Crimped metallic sleeve 34 defines an approximate diameter "b" which is less than diameter "a" of body 24. Medication such as insulin or heparin is pre-filled into vial 23 and is retained therein by a rubber stopper 36. Stopper 36 is in sliding fluid-tight engagement with the tubular wall of barrel 24. Distally directed forces on stopper 36 urge the medication from pen 11 as explained further below.

Figure 2:
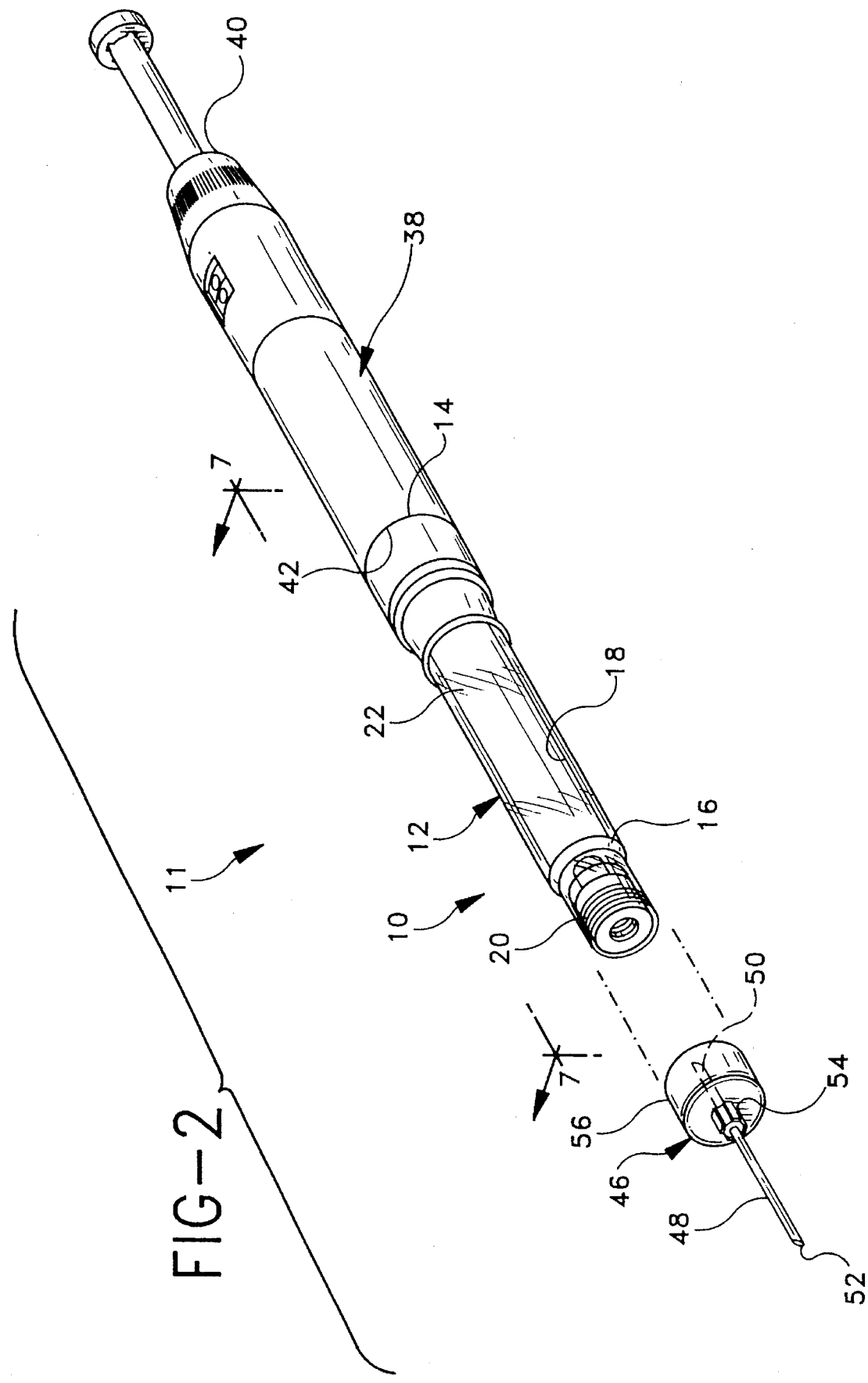
FIG. 2 is a perspective view of the assembled medication delivery pen incorporating the cartridge retainer assembly of the subject invention.

Medication delivery pen 11 further includes a prior art dosing apparatus identified generally by the numeral 38. Dosing apparatus 38 also is generally cylindrical and includes opposed proximal and distal ends 40 and 42 respectively. Threads are disposed at distal end 42 of prior art dosing apparatus 38 for releasable threaded engagement with proximal end 14 of body 12 of cartridge retainer assembly 10, as shown in FIG. 2. A plunger rod 44 projects distally from dosing apparatus 38 and is dimensioned to engage stopper 36 of cartridge assembly 22. The prior art dosing apparatus 38 includes known mechanisms therein for setting a selected dose of medication to be delivered by pen 11. A dispensing mechanism (not shown) is operative to drive plunger rod 44 a selected distance in a distal direction for moving stopper 36 a distance that will inject the selected dose of medication from cartridge assembly 22. Although a particular prior art dosing apparatus 38 is depicted in FIGS. 1 and 2, it is to be understood that other dosing apparatus can be used with the cartridge retainer assembly of the subject invention.

Medication delivery pen 11 further includes a prior art needle assembly 46 having a metallic needle cannula 48 with opposed proximal and distal tips 50 and 52 respectively and a lumen (not shown) extending entirely therethrough. A cork 54 is securely affixed at an intermediate position along needle cannula 48, and a cap 56 is securely affixed to cork 54. Cap 56 of prior art needle assembly 46 includes an array of internal threads (not shown) for removable mounting to cartridge retainer assembly 10.

As explained above, prior art cartridge assemblies 22 are subject to significant dimensional variation and eccentricities. In particular, the crimped mounting of metal sleeve 34 to neck 30 can result in diametrical or axially length differences from one cartridge to the next. Additionally, considerable eccentricities between neck 30 and body 24 are likely to exist.

Figure 3:
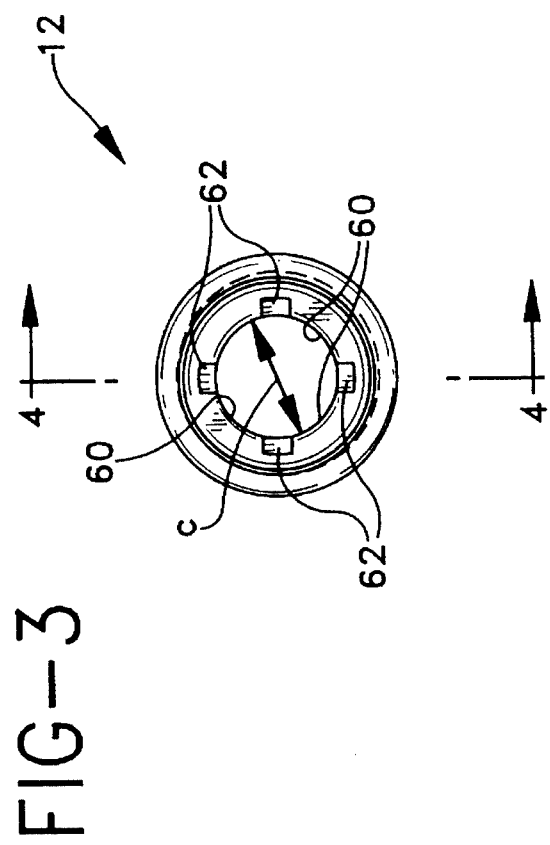
FIG. 3 is an end elevational view of the body of the cartridge retainer assembly.
Figure 4:
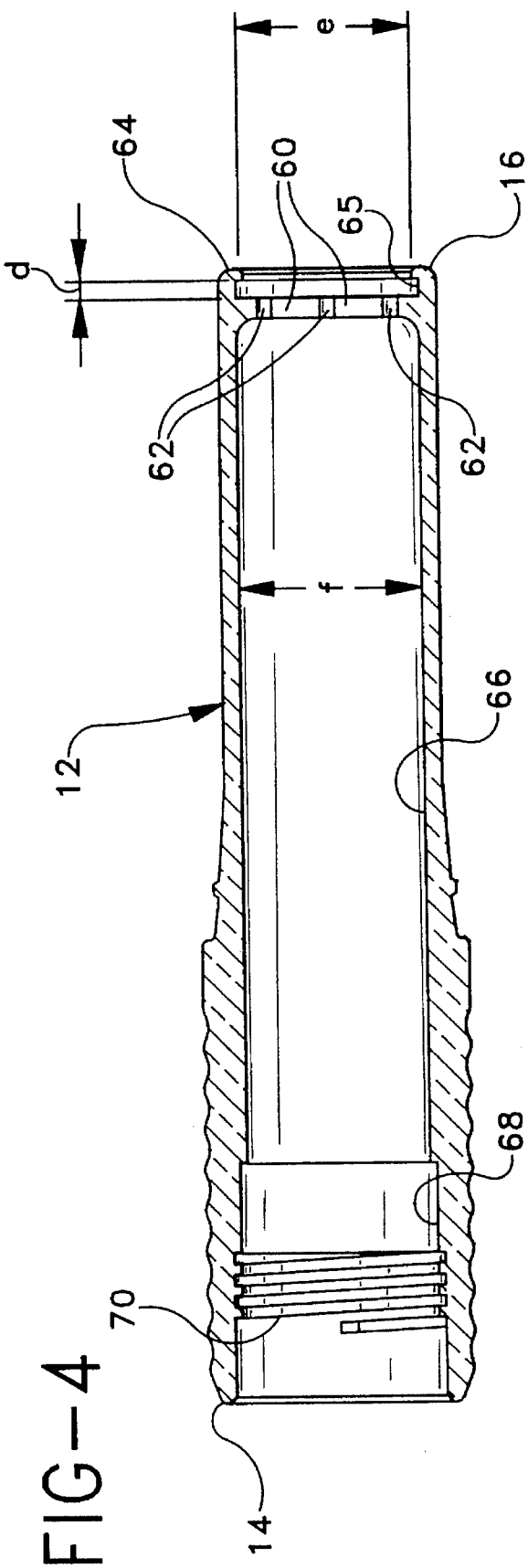
FIG. 4 is a cross-sectional view taken along line 4—4 in FIG. 3

Cartridge retainer assembly 10 accommodates the dimensional variations and eccentricities that exist in prior art cartridge assemblies 22. More particularly, as shown in FIGS. 3 and 4 body 12 of cartridge retainer assembly 10 includes a plurality of inwardly projecting supports 60 defining sections of arcs concentric with body 12. Supports 60 define an inside diameter "c" which is greater than diameter "b" defined by crimped sleeve 34 of cartridge assembly 22. Supports 60 are separated from one another by anti-rotation notches 62. An inwardly projecting annular rim 64 is defined at the extreme distal end 16 of body 12 and in spaced relation to the supports 60. Thus, an annular locking groove 65 with an axially measure thickness "d" and an inside diameter "e" is disposed intermediate supports 60 and rim 64.

Portions of body 12 disposed proximally of supports 60 define a vial receiving chamber 66 of substantially uniform diameter "f" which is slightly greater than diameter "a" of vial barrel 24. Portions of body 12 proximally of chamber 66 are of slightly larger diameter and define a recess 68 for receiving a portion of dosing apparatus 38. An array of internal threads 70 in recess 68 engage threads on proximal end 42 of dosing apparatus 38. It is to be understood, however, that other releasable engagement means between dosing apparatus 38 and cartridge retainer assembly 10 can be provided. For example, internal threads can be formed on dosing apparatus 38 and corresponding external threads can be defined on cartridge retainer assembly 10.

Figure 5:
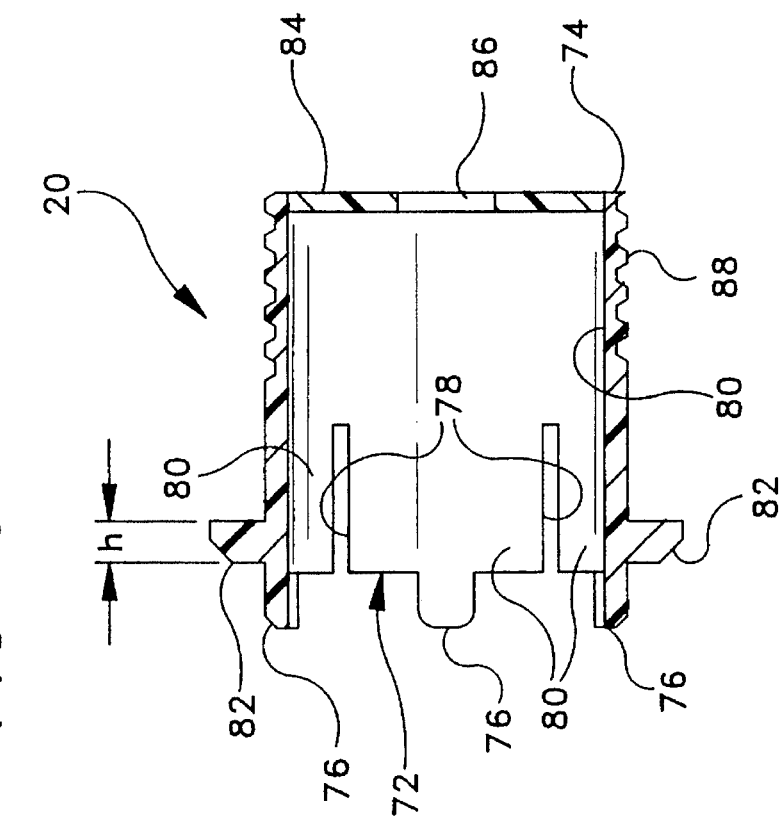
FIG. 5 is an end elevational view of the needle mounting collar of the cartridge retainer assembly.
Figure 6:
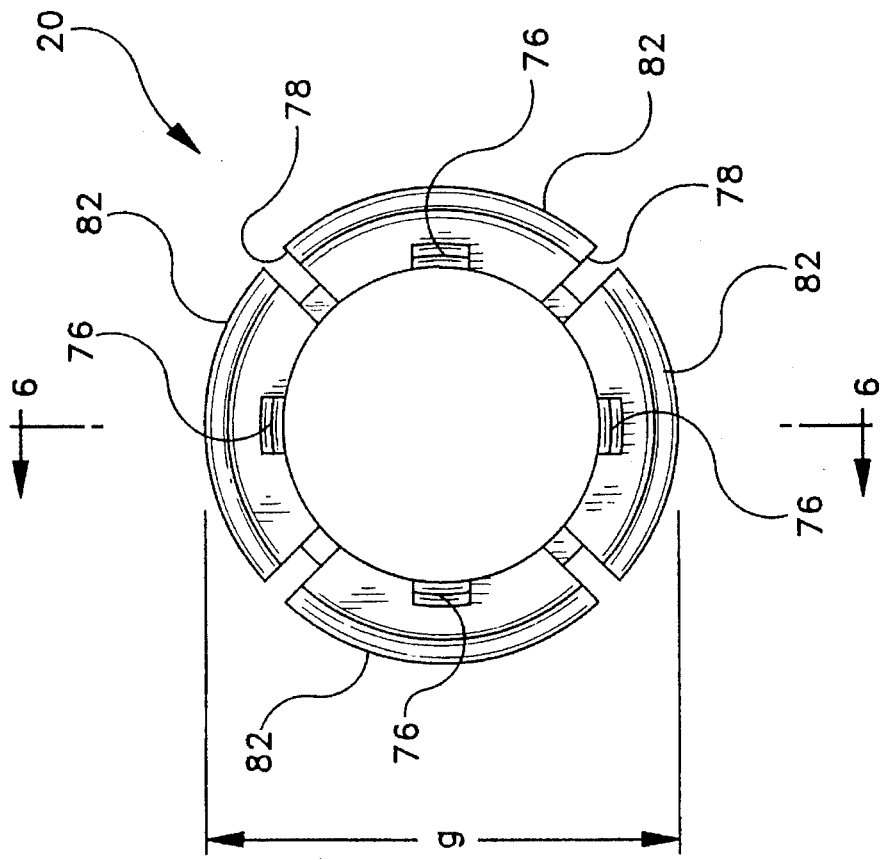
FIG. 6 is a cross-sectional view taken along line 6—6 in FIG. 5.

Needle mounting collar 20 of vial retainer assembly 10 includes opposed proximal and distal ends 72 and 74 respectively as shown in FIGS. 5 and 6. Proximal end 72 is characterized by a plurality of anti-rotation projections 76 dimensioned and disposed for sliding engagement in notches 62 between arcuate supports 60 near distal end 16 of cartridge retainer body 12.

Needle mounting collar 20 further includes a plurality of spaced apart axially aligned slots 78 extending from proximal end 72 toward distal end 74. Slots 78 define a plurality of proximally extending resiliently deflectable fingers 80 on proximal end 72 of collar 20.

Proximal portions of deflectable fingers 80 are characterized by outwardly projecting locking ridges 82. Each locking ridge 82 has an axially measured thickness "h" which is slightly less than the thickness "d" defined by locking groove 65 at distal end 16 of body 12. Opposed locking ridges 82 further define an outside diameter "g" approximately equal to or slightly less than the diameter "e" defined by locking groove 65 in body 12.

Distal end 74 of needle mounting collar 20 includes a generally annular end wall 84 having an aperture 86 extending therethrough for access by proximal point 50 of needle cannula 48. An array of outwardly disposed threads 88 is defined intermediate proximal and distal ends 72 and 74 respectively. Threads 88 are disposed and dimensioned for engaging threads on prior art needle assembly 46.

Needle mounting collar 20 and cartridge retainer body 12 are lockingly engaged with one another prior to sale of pen 11 by merely urging proximal end 72 of collar 20 into distal end 16 of body 12. This assembly is carried out by first aligning anti-rotation projections 76 at proximal end 72 of collar 20 with anti-rotation notches 62 between supports 60 at distal end 16 of body 12. After sufficient movement of collar 20 and body 12 toward one another, the chamfer on locking ridges 82 will engage annular rim 64 of body 12 to generate radially inward deflection of fingers 80. After sufficient movement of collar 20 and body 12 toward one another, locking ridges 82 will pass proximally beyond rim 64. Fingers 80 will then resiliently return toward an undeflected condition to lockingly engage ridges 82 in annular locking groove 65.

Assembly of medication delivery pen 11 continues by inserting cartridge 22 into cartridge retainer assembly 10. More particularly, neck 30 and crimped metallic sleeve 34 of vial 22 are inserted in a proximal to distal direction into open proximal end 14 of body 12 of the cartridge retainer assembly. Crimped metallic sleeve 34 eventually will pass entirely through body 12, and further advancement of cartridge 22 into cartridge retainer assembly 10 will require entry of crimped metallic sleeve 34 into needle mounting collar 20. As noted above, considerable dimensional variation and eccentricities between the neck and body of prior art vials are known to exist. If such eccentricities do exist, crimped metallic sleeve 34 will cause collar 20 to float radially relative to body 12 into a position that conforms with any dimensional inconsistencies or eccentricities in cartridge 22. More particularly, forces generated by the distal advancement of cartridge 22 will cause resiliently deflectable fingers 80 of needle mounting collar 20 to deflect into a position that conforms with the actual location and alignment of crimped metallic sleeve 34. This floating movement will cause needle mounting collar 20 and body 12 of cartridge retainer assembly 10 to assume an eccentric alignment that conforms with an eccentrically aligned neck and body on a vial.

Further distally directed movement of vial 22 into cartridge retainer assembly 10 will cause shoulder 28 of cartridge 22 to seat against arcuate supports 60 of body 12. Supports 60 define the fully seated position of cartridge 22 in cartridge retainer assembly 10 and function to securely engage vial 22. In this fully seated position, as shown most clearly in FIG. 7, septum 32 of cartridge 22 is spaced proximally from distal wall 84 of needle mounting collar 20.

Dosing apparatus 38 may next be assembled to proximal end 14 of the body of cartridge retainer assembly 10 such that plunger rod 44 of dosing apparatus 38 engages stopper 36 of cartridge 22.

Medication delivery pen 11 may be used by mounting a needle assembly 46 to needle mounting collar 20 of cartridge retainer assembly 10. This mounting is achieved by moving needle assembly 46 in a proximal direction over needle mounting collar 20 until the threads (not shown) of cap 56 engage external threads 88 on needle mounting collar 20. As noted above, threads 88 of needle mounting collar 20 are spaced from the extreme distal end of needle mounting collar 20. Thus, the initial axial advancement of cap 56 over needle mounting collar 20 will cause proximal point 50 of needle cannula 48 to pierce rubber septum 32 of cartridge 22 prior to rotational threaded engagement of needle assembly 46 with needle mounting collar 20. Thus, the bevel which defines proximal point 50 will advance axially through septum 32 without a rotation that could tear rubber septum 32. After threads of cap 56 engage threads 88 of needle mounting collar 20, further advancement of needle assembly 46 requires relative rotation between cap 56 and needle mounting collar 20. It will be appreciated that needle mounting collar 20 is too small to be readily griped by the user of medication delivery pen 11, and is partly covered by cap 56. However, the relative rotation can be achieved by rotating body 12 of cartridge retainer assembly 10. In particular, as noted above, anti-rotation projections 76 of needle mounting collar 20 are engaged in anti-rotation slots 62 which are defined between adjacent supports 60 of body 12. Hence, rotation of body 12 is transmitted to needle mounting collar 20 and enables complete rotational engagement of needle assembly 46.

Use of medication delivery pen 11 proceeds in a conventional manner with dosing apparatus 38. As explained above, actuation of dosing apparatus 10 causes liquid medication in cartridge 22 to be urged in a distal direction. The medication will be urged through the lumen of needle cannula 48. This distally directed liquid pressure also will cause septum 32 to distend in a distal direction. However, as noted above and as shown in FIG. 7, septum 32 is spaced proximally from cork 54 of needle assembly 46, and will not be urged into contact with cork 54. Thus, the drooling or weeping of liquid medication can be substantially prevented. This is enabled because cartridge 22 is supported and accurately positioned by engagement of vial shoulder 28 with supports 60 of body 12. Hence neck 30 and crimped metallic sleeve 34 need not be closely engaged by needle mounting collar 20.

After medication delivery pen 11 has been used, needle assembly 46 is separated from needle mounting collar 20 and discarded. The user is encouraged to apply a disinfectant to the distal end of medication delivery pen 11. Disinfectants have the potential of adversely affecting some plastic materials that could be used in a medication delivery pen. However, the two-part construction of vial retainer assembly 10 enables needle mounting collar 20 to be made from a metal or other material that is resistant to disinfectants that may be applied by the user.

What is claimed is:

1. A cartridge retainer assembly for retaining a medication cartridge having a barrel and a neck, said cartridge retainer assembly comprising:

a generally tubular body having opposed proximal and distal ends and being dimensioned for securely receiving a barrel of a cartridge therein;

a generally tubular needle mounting collar having opposed proximal and distal ends and being dimensioned for receiving a neck of the cartridge therein; and cooperating engagiment means on said needle mounting collar and said tubular body for preventing distal and proximal movement of said needle mounting collar with respect to said body and for providing transversely floatable engagement between said needle mounting collar and said body, whereby said engagement means enables said cartridge retainer assembly to accommodate dimensional variations and eccentricities of the cartridge when the neck of the cartridge is being inserted through said body and into said needle mounting collar.

2. The cartridge retainer assembly of claim 1, wherein said engagement means comprises a plurality of resiliently deflectable fingers on said needle mounting collar.

3. The cartridge retainer assembly of claim 2, wherein each of said resiliently deflectable fingers has a locking ridge thereon and wherein said engagement means further comprises a groove on said body engaging said locking ridges, said engagement of said locking ridges and said groove retain said needle mounting collar and said body in substantially fixed axial position relative to one another.

4. The cartridge retainer assembly of claim 1, wherein the engagement means of said needle mounting collar and said body further comprises means for preventing relative rotation between said needle mounting collar and said body.

5. The cartridge retainer assembly of claim 1, wherein said needle mounting collar and said body are formed from dissimilar materials.

6. The cartridge retainer assembly of claim 1, wherein said needle mounting collar comprises an array of external threads thereon for threadedly and releasably engaging a needle assembly, said threads on said needle mounting collar being disposed proximally of said distal end of said needle mounting collar.

7. A cartridge retainer assembly for retaining a medication cartridge having a barrel and a neck defining a smaller cross-section than the barrel, said cartridge retainer assembly comprising:

a generally tubular body having opposed proximal and distal ends and a chamber therebetween, said chamber being dimensioned and configured for engaging a barrel of a cartridge therein, said body further including at least one inwardly projecting support defining a distal end of said chamber and including at least one anti-rotation slot formed therein, and a annular rib spaced distally from said support and defining a locking groove therebetween;

a generally tubular needle mounting collar having opposed proximal and distal ends, said proximal end of said collar including at least one axially aligned anti-rotation projection engaged in said at least one slot for preventing rotation between said needle mounting collar and said body, an outwardly projecting locking ridge engaged in said locking groove of said body for preventing distal and proximal movement of said needle mounting collar with respect to said body, and a plurality of resiliently deflectable fingers defined by a corresponding plurality of axially aligned slots extending from said proximal end to a location intermediate said ends, said grooves permitting deflection of said fingers to accommodate dimensional inconsistencies and eccentricities of a barrel and a neck of the cartridge.

8. The cartridge retainer assembly of claim 7, wherein said body is formed from a transparent plastic material and wherein said needle mounting collar is formed from a metallic material.

9. The cartridge retainer assembly of claim 7, wherein said plurality of slots on said needle mounting collar includes four slots extending into said proximal end and defining four resiliently deflectable fingers, said needle mounting collar further including said at least one anti-rotation projection comprising four anti-rotation projections disposed respectively at central positions on each said resiliently deflectable finger.

* * * * *